US009889063B2

(12) United States Patent
Wright et al.

(10) Patent No.: US 9,889,063 B2
(45) Date of Patent: Feb. 13, 2018

(54) METHODS AND SYSTEMS FOR DETERMINING USE COMPLIANCE OF A COMPRESSION THERAPY DEVICE

(71) Applicant: Wright Therapy Products, Inc., Oakdale, PA (US)

(72) Inventors: Carol L. Wright, Pittsburgh, PA (US); Gregory Yurko, Murrysville, PA (US)

(73) Assignee: WRIGHT THERAPY PRODUCTS, INC., Oakdale, PA (US)

( * ) Notice: Subject to any disclaimer, the term of this patent is extended or adjusted under 35 U.S.C. 154(b) by 383 days.

(21) Appl. No.: 13/915,458

(22) Filed: Jun. 11, 2013

(65) Prior Publication Data

US 2013/0331748 A1 Dec. 12, 2013

Related U.S. Application Data

(60) Provisional application No. 61/658,204, filed on Jun. 11, 2012.

(51) Int. Cl.
*A61H 9/00* (2006.01)
*G06F 19/00* (2018.01)
*G06Q 50/24* (2012.01)

(52) U.S. Cl.
CPC ....... *A61H 9/0007* (2013.01); *G06F 19/3481* (2013.01); *G06Q 50/24* (2013.01);
(Continued)

(58) Field of Classification Search
CPC ....... G06Q 50/22; G06Q 50/24; A61H 9/0078
See application file for complete search history.

(56) References Cited

U.S. PATENT DOCUMENTS 3,811,431 A   5/1974   Apstein
4,011,860 A   3/1977   Lee
(Continued)

FOREIGN PATENT DOCUMENTS

DE   19846922 A1   4/2000
FR   2682279 A1    4/1993
(Continued)

OTHER PUBLICATIONS

Motorola, Integrated silicone Pressure Sensor On-Chip Signal Conditioned, Temperature Compensated and Calibrated; MPX5050 MPXV5050G Series, 2002.
(Continued)

*Primary Examiner* — Linh Giang Le
(74) *Attorney, Agent, or Firm* — Shumaker, Loop & Kendrick, LLP

(57) ABSTRACT

Methods and systems are disclosed for determining patient compliance for using a compression therapy device. The systems may include a compression therapy sleeve and a controller having a non-transitory memory device. During a therapy session, the controller may record in the memory device operational therapy data obtained from sensors associated with the controller and/or sleeve. The controller may calculate a compliance metric based in part on the therapy data. The controller may then communicate the data or metric to one or more recipients. The methods may include allowing the patient to transfer a removable memory device from the controller to a personal computer, and uploading the therapy data or metric stored on it to a recipient website. Alternative methods may include the patient receiving the metric from the controller at the end of the therapy session, and then providing the metric to a recipient by phone.

25 Claims, 5 Drawing Sheets

(52) U.S. Cl.
CPC .... *A61H 9/0078* (2013.01); *A61H 2201/5002* (2013.01); *A61H 2201/5012* (2013.01); *A61H 2201/5071* (2013.01); *A61H 2201/5097* (2013.01)

(56) References Cited

U.S. PATENT DOCUMENTS

| | | | |
|---|---|---|---|
| 4,011,866 A | 3/1977 | Klein et al. | |
| 4,013,069 A | 3/1977 | Hasty | |
| 4,086,920 A | 5/1978 | Miniere | |
| 4,338,923 A | 7/1982 | Gelfer et al. | |
| 4,424,806 A | 1/1984 | Newman et al. | |
| 4,762,121 A | 8/1988 | Shienfeld | |
| 4,773,397 A | 9/1988 | Wright et al. | |
| 4,865,020 A | 9/1989 | Bullard | |
| 4,922,893 A | 5/1990 | Wright et al. | |
| 5,014,681 A | 5/1991 | Heeman et al. | |
| 5,092,317 A | 3/1992 | Zelikovski | |
| 5,117,812 A | 6/1992 | McWhorter | |
| 5,179,941 A | 1/1993 | Siemssen et al. | |
| 5,186,163 A | 2/1993 | Dye | |
| 5,263,473 A | 11/1993 | McWhorter | |
| 5,307,791 A | 5/1994 | Senoue et al. | |
| 5,383,842 A | 1/1995 | Bertini | |
| 5,437,610 A | 8/1995 | Cariapa et al. | |
| 5,496,262 A | 3/1996 | Johnson, Jr. et al. | |
| 5,554,103 A | 9/1996 | Zheng et al. | |
| 5,571,075 A | 11/1996 | Bullard | |
| 5,575,762 A | 11/1996 | Peeler et al. | |
| 5,584,798 A | 12/1996 | Fox | |
| 5,588,955 A | 12/1996 | Johnson, Jr. et al. | |
| 5,591,200 A | 1/1997 | Cone et al. | |
| 5,795,312 A | 8/1998 | Dye | |
| 5,830,164 A | 11/1998 | Cone et al. | |
| 5,840,049 A | 11/1998 | Tumey et al. | |
| 5,843,007 A | 12/1998 | McEwen et al. | |
| 5,891,065 A | 4/1999 | Cariapa et al. | |
| 5,951,502 A | 9/1999 | Peeler et al. | |
| 5,968,073 A | 10/1999 | Jacobs | |
| 6,007,559 A | 12/1999 | Arkans | |
| 6,010,471 A | 1/2000 | Ben-Noon | |
| 6,080,120 A | 6/2000 | Sandman et al. | |
| 6,123,681 A | 9/2000 | Brown, III | |
| 6,129,688 A | 10/2000 | Arkans | |
| 6,135,116 A | 10/2000 | Vogel et al. | |
| 6,179,796 B1 | 1/2001 | Waldridge | |
| 6,231,532 B1 | 5/2001 | Watson et al. | |
| 6,234,532 B1 | 5/2001 | Watson et al. | |
| 6,290,662 B1 | 9/2001 | Morris et al. | |
| 6,296,617 B1 | 10/2001 | Peeler et al. | |
| 6,315,745 B1 | 11/2001 | Kloecker | |
| 6,406,445 B1 | 6/2002 | Ben-Nun | |
| 6,436,064 B1 | 8/2002 | Kloecker | |
| 6,440,093 B1 | 8/2002 | McEwen et al. | |
| 6,494,852 B1 | 12/2002 | Barak et al. | |
| 6,544,202 B2 | 4/2003 | McEwen et al. | |
| 6,558,338 B1 | 5/2003 | Wasserman | |
| 6,585,669 B2 | 7/2003 | Manor et al. | |
| 6,645,165 B2 | 11/2003 | Waldridge et al. | |
| 6,736,787 B1 | 5/2004 | McEwen et al. | |
| 6,786,879 B1 | 9/2004 | Bolam et al. | |
| 6,846,295 B1 | 1/2005 | Ben-Nun | |
| 6,852,089 B2 | 2/2005 | Kloecker et al. | |
| 6,860,862 B2 | 3/2005 | Waldridge et al. | |
| 6,884,255 B1 | 4/2005 | Newton | |
| 6,893,409 B1 | 5/2005 | Lina | |
| 6,945,944 B2 | 9/2005 | Kuiper et al. | |
| 6,966,884 B2 | 11/2005 | Waldridge et al. | |
| 7,048,702 B2 | 5/2006 | Hui | |
| 7,074,200 B1 | 7/2006 | Lewis | |
| 7,063,676 B2 | 8/2006 | Barak et al. | |
| 7,398,803 B2 | 7/2008 | Newton | |
| 7,637,879 B2 | 12/2009 | Barak et al. | |
| 7,846,114 B2 | 12/2010 | Webster et al. | |
| 7,862,525 B2 | 1/2011 | Carkner et al. | |
| 2002/0091345 A1 | 7/2002 | Hazard | |
| 2003/0208465 A1 | 11/2003 | Yurko et al. | |
| 2004/0059274 A1 | 3/2004 | Kloecker et al. | |
| 2004/0171971 A1 | 9/2004 | Ravikumar et al. | |
| 2004/0261182 A1 | 12/2004 | Biggie et al. | |
| 2005/0154336 A1 | 7/2005 | Kloecker et al. | |
| 2005/0159690 A1* | 7/2005 | Barak | A61H 9/0078 601/149 |
| 2005/0222526 A1 | 10/2005 | Perry et al. | |
| 2006/0161081 A1 | 7/2006 | Barak et al. | |
| 2006/0272719 A1 | 12/2006 | Steinberg | |
| 2007/0049853 A1 | 3/2007 | Adams et al. | |
| 2007/0088239 A1 | 4/2007 | Roth et al. | |
| 2007/0272250 A1 | 11/2007 | Lewis | |
| 2008/0146980 A1* | 6/2008 | Rousso | A61H 11/02 601/152 |
| 2008/0281240 A1 | 11/2008 | Wright et al. | |
| 2009/0007341 A1 | 1/2009 | Roff et al. | |
| 2009/0056020 A1 | 3/2009 | Caminade et al. | |
| 2009/0145234 A1 | 6/2009 | Gasbarro et al. | |
| 2012/0065561 A1 | 3/2012 | Ballas et al. | |
| 2012/0219432 A1 | 8/2012 | Wright et al. | |
| 2012/0277636 A1 | 11/2012 | Blondheim et al. | |
| 2013/0125613 A1 | 5/2013 | Grotov | |
| 2013/0237889 A1 | 9/2013 | Wright et al. | |
| 2014/0052028 A1 | 2/2014 | Wright et al. | |
| 2015/0150746 A1 | 6/2015 | Yurko et al. | |
| 2015/0202116 A1 | 7/2015 | Wright | |
| 2015/0224012 A1 | 8/2015 | Wright et al. | |

FOREIGN PATENT DOCUMENTS

| | | | |
|---|---|---|---|
| GB | 2313784 A | 10/1997 | |
| WO | WO 2005/082314 A1 | 9/2005 | |
| WO | WO 2007/074451 A2 | 7/2007 | |
| WO | WO 2009/076269 A2 | 6/2009 | |
| WO | WO 2013/138307 A1 | 9/2013 | |
| WO | WO 2014/031409 A1 | 2/2014 | |
| WO | WO 2015/084312 A1 | 6/2015 | |

OTHER PUBLICATIONS

Extended European Search Report for EP 13760396 dated Sep. 30, 2015.

* cited by examiner

METHODS AND SYSTEMS FOR DETERMINING USE COMPLIANCE OF A COMPRESSION THERAPY DEVICE

CLAIM OF PRIORITY

This application claims the benefit of U.S. Provisional Application Ser. No. 61/658,204 filed Jun. 11, 2012, the disclosure of which is incorporated by reference herein in its entirety.

BACKGROUND

Diseases such as venous insufficiency, lymphedema, and other edematous conditions can often result in the pooling of bodily fluids in areas of the body distal from the heart. Venous insufficiency can result when the superficial veins of an extremity empty into the deep veins of the lower leg. Normally, the contractions of the calf muscles act as a pump, moving blood into the popliteal vein, the outflow vessel. Failure of this pumping action can occur as a result of muscle weakness, overall chamber size reduction, valvular incompetence, and/or outflow obstruction. Each of these conditions can lead to venous stasis and hypertension in the affected area. Lymphedema, which is swelling due to a blockage of the lymph passages, may be caused by lymphatic obstruction, a blockage of the lymph vessels that drain fluid from tissues throughout the body. This is most commonly due to cancer surgery, general surgery, tumors, radiation treatments, trauma and congenital anomalies. Lymphedema is a chronic condition that currently has no cure.

Fluid accumulation can be painful and debilitating if not treated. Fluid accumulation can reduce oxygen transport, interfere with wound healing, provide a medium that support infections, or even result in the loss of a limb if left untreated.

Compression therapy devices are often used in the treatment of venous insufficiency by moving the accumulated bodily fluids. Additional conditions may also benefit from the use of compression therapy devices. Such devices typically include an air compressor that may blow air through tubes to an appliance such as a sleeve or boot containing a number of separately inflatable cells that is fitted over a problem area (such as an extremity or torso). Such devices may also include pneumatic components adapted to inflate and exhaust the cells, and control circuitry governing the pneumatic components. A therapeutic cycle or protocol may involve, for example, sequential inflation of the cells to a pre-set pressure in a distal to a proximal order, followed by exhausting all the cells in concert.

Multiple compression therapy sessions may be required to help maintain proper fluid flow in the patient over time. While such therapy sessions may be provided under supervision by a therapist or physician at a clinic or hospital, it may be more practical to have the patient self-administer the therapy at home using rented therapy equipment. Home therapy has the advantage of being more convenient for the patient, who may schedule the therapy sessions at will and who will not need to travel to a medical facility for the sessions. In addition, home therapy has the economic advantage of not requiring the time and resources of either medical personnel or facilities.

A potential disadvantage of home therapy, however, is a lack of patient compliance. A therapeutic session may be uncomfortable, and a patient may not feel motivated to take time from his or her schedule to perform the therapy. Patient compliance is important to several parties associated with the therapy. The manufacturer or supplier of the equipment may want to monitor patient use of the equipment as part of ongoing post-sales quality assurance. The physician and/or therapist may want to monitor compliance as part of their overall monitoring of patient health. By assessing a patient's health status over time and knowing the level of patient therapy compliance, a physician may be able to determine if a change in the therapeutic protocol may be required. In addition, health insurers may reimburse the companies providing the therapeutic device and/or disposable items associated with it. The insurers, however, may reimburse for equipment rentals only if the equipment is actually in use. Other individuals and organizations may have an interest in patient compliance, including, as non-limiting examples, researchers, family members, clinical trial registries, and accountable care organizations (ACO). It is therefore important to assure patient compliance in using such a compression therapy device.

SUMMARY

Before the present methods, systems and materials are described, it is to be understood that this disclosure is not limited to the particular methodologies, systems and materials described, as these may vary. It is also to be understood that the terminology used in the description is for the purpose of describing the particular versions or embodiments only, and is not intended to limit the scope.

It must also be noted that as used herein and in the appended claims, the singular forms "a," "an," and "the" include plural references unless the context clearly dictates otherwise. Thus, for example, reference to a "valve" is a reference to one or more valves and equivalents thereof known to those skilled in the art, and so forth. Unless defined otherwise, all technical and scientific terms used herein have the same meanings as commonly understood by one of ordinary skill in the art. Although any methods, materials, and devices similar or equivalent to those described herein can be used in the practice or testing of embodiments, the preferred methods, materials, and devices are now described. All publications mentioned herein are incorporated by reference. Nothing herein is to be construed as an admission that the embodiments described herein are not entitled to antedate such disclosure by virtue of prior invention.

In an embodiment, a method of monitoring a therapy compliance by at least one patient includes providing a compression therapy device, causing the compression therapy device to execute at least one compression therapy protocol, identifying, by at least one sensor, operational therapy data during the at least one compression therapy protocol, storing, by at least one memory storage device, the operational therapy data during the at least one compression therapy protocol, calculating, by a controller, a metric of patient compliance based at least in part on the operational therapy data, and transmitting, by the controller, the metric of patient compliance to at least one compliance data recipient. The compression therapy device may include an inflatable compression sleeve, a source of fluid for inflating the compression sleeve, and a controller for controlling the inflation of the compression sleeve. The controller may further include at least one sensor associated with the compression sleeve, at least one non-transitory memory storage device, and at least one communication device.

In some embodiments, transmitting the metric of patient compliance may include activating, by the at least one patient, a user input interface device associated with the controller, receiving, by the at least one patient, the metric of patient compliance from a user output interface device associated with the controller, and communicating, by the at least one patient, the metric of patient compliance to the at least one compliance data recipient.

In some embodiments, transmitting the metric of patient compliance may include one or more of removing a removable data storage device from the controller and placing the removable data storage device in data communication with a computing device that is further in data communication with an electronic device controlled at least in part by the at least one compliance data recipient, transmitting the metric over an Ethernet connection to a computing device in data communication with a website controlled at least in part by the at least one compliance data recipient, transmitting the metric via an infrared connection device to a computing device in data communication with a website controlled at least in part by the at least one compliance data recipient, transmitting the metric via a serial connection to a computing device in data communication with a website controlled at least in part by the at least one compliance data recipient, transmitting the metric via a serial connection to a telephony device in data communication with the at least one compliance data recipient, transmitting the metric via a localized personal area network to a telephony device in data communication with the at least one compliance data recipient, transmitting the metric via a wireless local area network to an electronic device controlled at least in part by the at least one compliance data recipient, and mailing a printed copy of the metric to the at least one compliance data recipient.

In some embodiments, a method of monitoring a therapy compliance by at least one patient may further include receiving, by a first compliance data recipient, a plurality of metrics of patient compliance, in which each metric is received from one of a plurality of patients, compiling a report, by the first compliance data recipient, based at least in part on the plurality of metrics, and transmitting, by the first compliance data recipient to a second compliance data recipient, the report.

BRIEF DESCRIPTION OF THE DRAWINGS

Aspects, features, benefits and advantages of the embodiments described herein will be apparent with regard to the following description, appended claims and accompanying drawings where:

SUMMARY

Figure 1A:
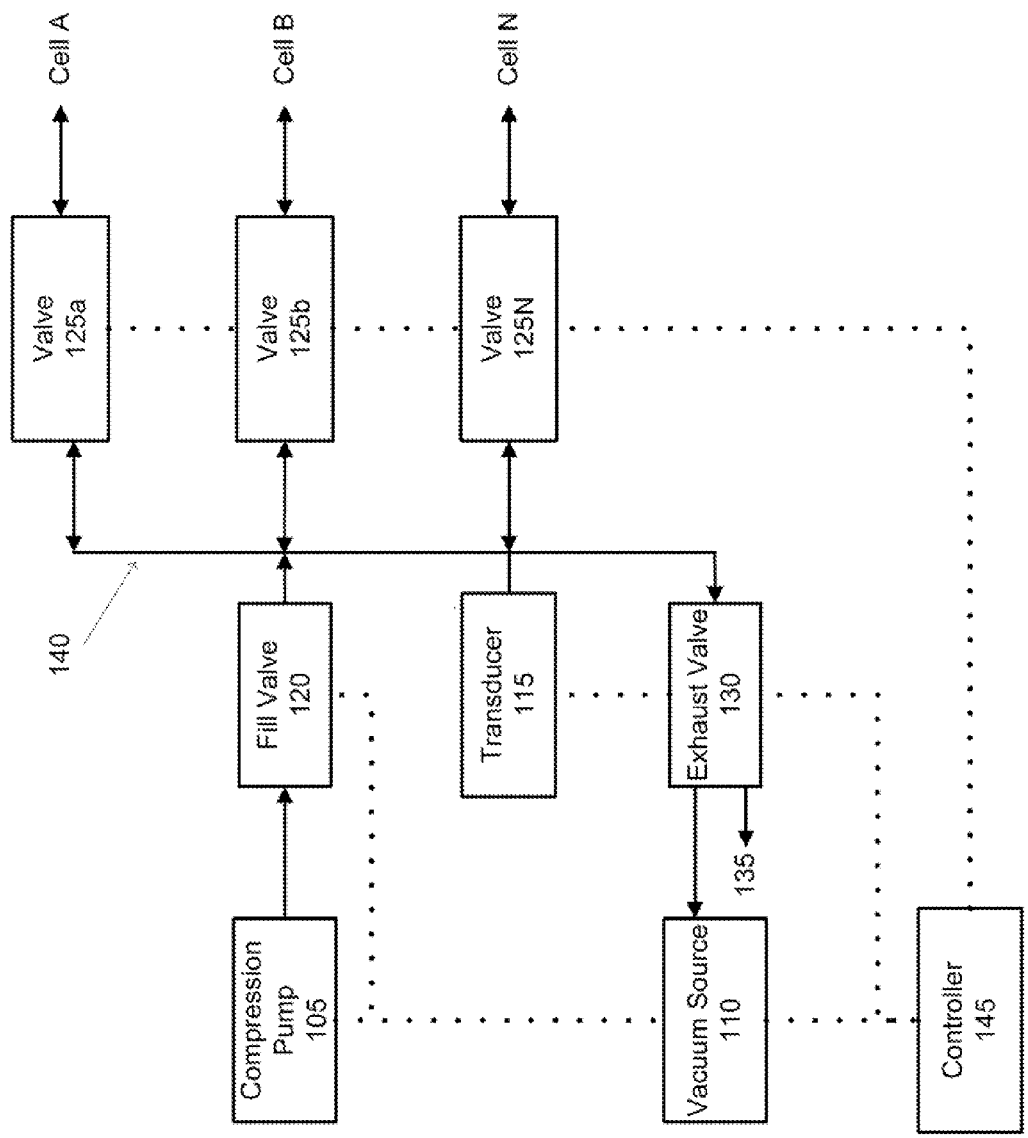
FIGS. 1a,b depict illustrative pneumatic compression therapy systems in accordance with embodiments.

For the purpose of this disclosure, the term "therapy data", may be defined as all data associated with a therapeutic session, including, but not limited to, data associated with time, date, pressure, air or fluid flow, temperature, patient ID, device type, sleeve type, device serial number, presence or absence of the treated body part, body part size, number of protocol repetitions during a clinical therapy session, and duration of each protocol repetition. The data may be represented in any fashion including, but not limited to, text, numerical values, and graphical representations such as charts or graphs.

For the purpose of this disclosure, the terms "therapy protocol" and "protocol" may be defined as a defined sequence of inflations and deflations of one or more inflatable cells associated with a compression sleeve. One or more cells may be inflated and/or deflated separately or simultaneously, synchronously or asynchronously.

For the purpose of this disclosure, the term "therapy session" may be defined a sequence of one or more therapy protocols that a patient may undergo as part of a compression therapy program. The therapy session may be based on a patient wearing one or more compression appliances or sleeves on at least one body part while one or more compression therapy protocols are executed by the therapy device. The session may include several repetitions of the same protocol, or a sequence of different protocols.

For the purpose of this disclosure, the term "patient compliance" may be defined as a condition in which a patient of a compression therapy session properly uses the compression therapy device for the entirety of the session. Proper use may include, without limitation, affixing the compression sleeve correctly about the body part to receive the therapy, activating the proper therapy protocol, and retaining the compression sleeve about the body part for the entire duration of the session. A compliant patient may be one who undergoes a therapy session or sessions using the compression device correctly and for the entire duration of the session. A non-compliant patient is one who may cause the compression therapy device to run a protocol without affixing the sleeve to the body part or affixing the sleeve incorrectly to the body part. A partially compliant patient may be one who properly affixes the compression sleeve to the body part requiring therapy, but who does not keep the body part within the sleeve for the entire duration of the therapeutic session. Information regarding partial patient compliance may provide a useful indicator to a medical professional that the therapy may be alleviating some of the patient's symptoms, and that shorter therapy sessions may be sufficient. Alternatively, a partially compliant patient may be one who finds the compression sleeve sufficiently uncomfortable. Such information may be useful to the device manufacturer who may use this information to improve the design of the compression therapy device or the compression sleeve.

For the purpose of this disclosure, the term "compression sleeve" may be defined as an inflatable appliance consisting of one or more inflatable chambers or cells used for delivering at least some compressive force to some tissue of a patient to relieve a medical condition. The sleeve may encompass one body part such as the chest, or two or more non-contiguous or contiguous body parts such as a combination of foot, ankle, calf (lower leg), and thigh (upper leg). Other non-limiting examples of compression sleeves may include appliances to treat the lower arm, the upper arm, the wrist, the hand, a combination of hand/wrist/lower arm/upper arm, chest, single shoulder, back, combination shoulder/chest/back, combination shoulder/chest/back/upper arm, abdomen, buttocks, and genitals. More than one compression sleeve may be worn by the patient at any one time.

Although the devices, systems, methods, illustrations, and examples disclosed herein may focus primarily on applications related to human patients, the devices, systems, methods, illustrations, and examples may equally apply to non-human animals that may benefit from an application of compression therapy for veterinary purposes.

FIGS. 1a,b depict embodiments of a pneumatic compression device. As shown in FIG. 1a, the pneumatic compression device may include a compression pump 105, a fill valve 120, a vacuum source 110, an exhaust valve 130, a transducer 115, a controller 145 and a plurality of cell valves, such as 125a-N. The compression pump 105 may be used to provide a pressurized fluid, including, without limitation, air, nitrogen, or water. The fill valve 120 may be in fluid connection with the compression pump 105 to receive the pressurized fluid. During an inflation period, the fill valve 120 may open to connect the output of the compression pump 105 to a common node or manifold 140. During a deflation period, exhaust valve 130 may open to connect the common manifold 140 to, for example, a vacuum source 110 to depressurize the cells. Alternatively, exhaust valve 130 may be connected to atmosphere 135. Typically, fill valve 120 and exhaust valve 130 may not be open at the same time. However, some modes of use of the compression device may benefit from the fill valve 120 and exhaust valve 130 being open together. Although FIG. 1a illustrates a single exhaust valve 130 capable of connecting to either a vacuum source 110 or the atmosphere 135, it may be appreciated that one exhaust valve may be used to connect the manifold 140 to the vacuum source 110, while a second exhaust valve may be used to connect the manifold 140 to atmosphere 135. Fill valve 120 and exhaust valve 130 may be manually operated, or may be automatically operated by controller 145. In an alternative embodiment, controller 145 may further include one or more communications links to one or more local or remote devices. Such communications links may permit, as one non-limiting example, a physician or therapist to direct, control, or monitor the pneumatic compression device. Additional fill and/or exhaust valves may be associated with the manifold 140. Each of the cell valves 125a-N may be connected to the common manifold 140 on a first side and a corresponding cell on a second side. Each cell valve 125a-N may be used to selectively connect (in an open configuration) or disconnect (in a closed configuration) the corresponding cell to the common manifold 140. Cell valves 125a-N may also be manually operated or automatically operated by controller 145.

The transducer 115 may be connected to and used to monitor the pressure of the common manifold 140. The controller 145 may receive information regarding the pressure detected by the transducer 115. Based on at least the received pressure information, the controller 145 may determine whether to open or close the fill valve 120, the exhaust valve 130, and/or one or more of the cell valves 125a-N.

In an embodiment, illustrated in FIG. 1a, the transducer 115 may have a transfer function associated with it which may be used to determine the input pressure monitored at the common manifold 140.

Figure 1B:
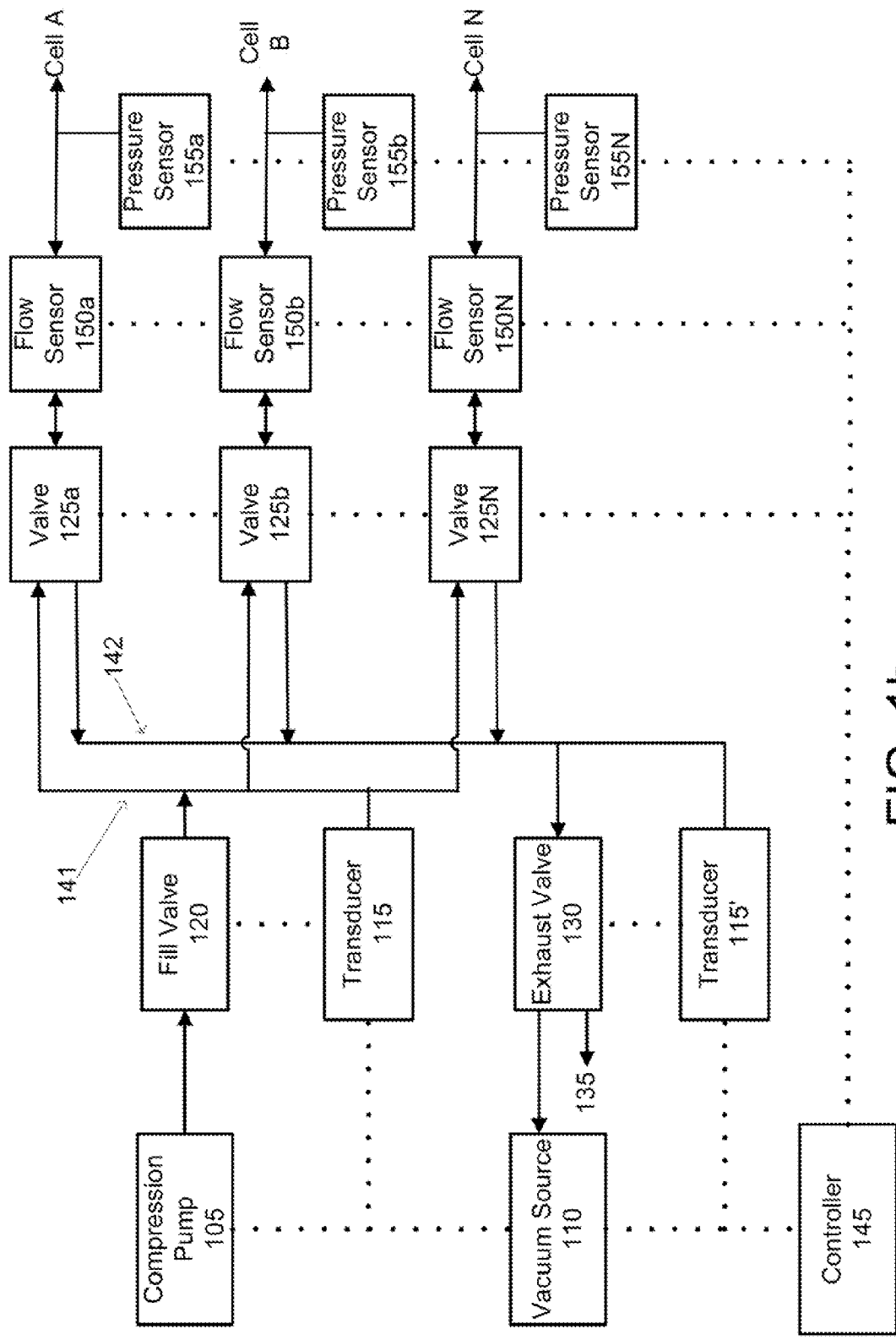

An additional embodiment is illustrated in FIG. 1b. In this embodiment, a fill manifold 141 may be associated with the fill valve 120 and compression pump 105. A separate exhaust manifold 142 may be associated with the vacuum source 110 and exhaust valve 130. Cell valves 125a-N may be associated with both the fill manifold 141 and exhaust manifold 142. It is understood that cell valves 125a-N in this embodiment may have a 3-way function: open to fill, open to exhaust, and closed. In an alternative embodiment, each cell may have a first valve to connect to the fill manifold 141 and a second valve to connect to the exhaust manifold 142.

In the dual manifold embodiment in FIG. 1b, transducer 115, associated with fill manifold 141, may be calibrated with respect to atmosphere by means of a separate shunt valve (not shown) associated either directly with transducer 115 or with the fill manifold 141. Exhaust manifold 142 may also be in communication with its own transducer 115' to monitor the pressure within the exhaust manifold. Transducers 115 and 115' may provide sensor data as well to controller 145.

In addition, each valve 125a-N may be in fluid connection with a flow sensor 150a-N in-line with the connection to its respective cell. Flow sensors 150a-N may provide sensor data as well to controller 145. For example, a flow sensor 150a-N may be used to monitor that its respective valve 125a-N is completely open. If a valve is blocked or otherwise impeded, the fluid flow through it may not match an expected flow profile as determined by controller 145. A flow sensor 150a-N could provide the controller 145 with data to indicate a fault with the associated valve 125a-N. The controller 145 may then be programmed to notify a user of the valve flow fault condition. Additionally, the flow sensors 150a-N may be used to accurately determine the rate of air flow into or from a particular cell, or the total amount of air pumped into (or exhausted from) a cell over a fixed period of time. Based on the data from the flow sensor 150a-N, the fill/exhaust rate for a cell may be adjusted by controller 145 to control the amount of time required for a fill or exhaust step. A clinician developing a particular therapy protocol may then be able to program a fill or exhaust time as part of the protocol. Such time-based programming may be easier for a clinician to use instead of flow rates and volumes.

Additionally, a pressure sensor 155a-N may be associated with each cell to measure the fluid pressure within the cell during its operation. The pressure sensors 155a-N may also provide data to controller 145 so that the controller may be able to control the operation of the compression device. A pressure sensor 155a-N associated with its respective cell, may provide direct indication of a pressurization or depressurization profile of the cell. Alternatively, transducer 115 may measure the pressure of any cell communicating with common manifold 140 by means of its respective valve 125a-N. Controller 145 may compare an individual cell pressure against a pre-programmed cell pressure profile. If a cell is unable to sustain an expected pressure, a leak condition may be determined. The controller 145 may then be programmed to notify a user of the leak condition.

Although FIG. 1a does not explicitly illustrate the use of either flow or pressure sensors between the valves 125a-N and their respective cells, it may be appreciated that either flow sensors, pressure sensors, or both types of sensors may be included in alternative embodiments. Similarly, although FIG. 1b illustrates the use of such sensors, it should be understood that other embodiments may lack either one or both types of sensors.

The pneumatic compression device may be operated to provide a variety of therapeutic protocols. A therapeutic protocol may be defined as a specific sequence of operations to inflate (fill) and deflate (exhaust) one or more cells while they are in contact with a patient. Therapeutic protocols may include, in a non-limiting example, a list of a sequence of cells to be activated, an inflation or deflation pressure measure for each cell, an amount of time during cell inflation or deflation, and a time between sequential cell activation.

Prior to the start of a therapeutic protocol, an initialization sequence may occur. In one example of an initialization sequence, fill valve 120 may be closed, thereby isolating the compression pump 105 from a manifold (either 140 or 141), and exhaust valve 130 may be opened to atmosphere 135.

The cell valves 125a-N may then be opened thereby placing each cell in fluid communication with either the common manifold 140 or exhaust manifold 142. In this manner, all the cells to be vented to the atmosphere. Alternatively, exhaust valve 130 may be opened to vacuum source 110 to permit rapid evacuation of the cells. The controller 145 may determine whether a minimum pressure threshold has been reached based on information received from the transducer 115 (for a common manifold configuration) or from transducer 115' (for a dual manifold configuration). The controller 145 may also receive sensor data from the cell specific pressure sensors 155a-N. In one embodiment, when the minimum pressure threshold is reached, the controller 145 may send operation commands to exhaust valve 130 to close. In another embodiment, the controller 145 may also provide operation commands to the cell valves 125a-N to close. In yet another embodiment, the controller 145 may initiate a therapeutic protocol. It may be appreciated that the initialization sequence may occur while the cells are in contact with the patient, before the cells are affixed onto the patient, or after a protocol has been completed.

A protocol may incorporate one or more cell fill phases. As a non-limiting example of such a fill phase, the following operating sequence may occur. One or more cell valves 125a-N may be opened along with the fill valve 120 thereby allowing the one or more cells to be in fluid communication with the compression pump 105. In an embodiment incorporating a common manifold 140, one or more of the cell valves 125a-N may open to the common manifold. In an embodiment having independent fill 141 and exhaust 142 manifolds, one or more of the cell valves 125a-N may be configured to open the cells to communicate with the fill manifold 141 only. In an embodiment, a cell valve, such as 125a, connected to a cell affixed to a distal portion of the patient, may be opened or remain open to the fill manifold 141 or common manifold 140 for inflation while cell valves associated with more proximal cells are closed to that manifold. The cell (e.g. cell A) connected to the open cell valve (e.g. 125a) may inflate as a result of being connected to the pressurized fluid from the compression pump 105. The cell pressure may be monitored by the controller 145 via the transducer 115 and/or a pressure sensor 155a associated specifically with that cell.

In an embodiment, the amount of pressure sensed by the transducer 115 may differ from the cell pressure at a particular cell. For example, pressure losses may occur between the transducer 115 and a cell. Accordingly, the controller 145 may access a lookup table to determine the threshold at which the pressure sensed by the transducer 115 is appropriate to close the cell valve 125a-N corresponding to the cell.

In another embodiment of a fill phase, an opened cell valve, such as 125a, may be modulated to control the fill rate of the corresponding cell. The opened cell valve may be modulated based on time and/or pressure. For example, a cell valve that is being modulated on a time basis may be opened for a first period of time and closed for a second period of time as the cell is inflating. Alternately, a cell valve that is being modulated on a pressure basis may be opened while the cell pressure increases and closed for a period of time during the inflation cycle. The pressure increase may be determined by measuring an initial cell pressure before opening the cell valve and the cell pressure as the cell valve is open. When the difference between the initial cell pressure and the inflating cell pressure is substantially equal to a specific value, the cell valve may be closed. The duty cycle at which the cell valve is modulated may be any value and may be specifically programmed by a user or clinician. The controller 145 may determine when to open and close the cell valve. For pressure-based modulation, any one or more of transducer 115 or cell specific pressure sensors 155 may provide pressure data to the controller 145 to assist in determining when to open and/or close the cell valve during modulation.

Modulation may be performed to ensure that the cell pressure does not increase too quickly for a given protocol. For example, a lymphedema patient may be treated with a protocol requiring slowly inflating and deflating cells. Alternatively, an arterial patient may require a protocol capable of rapid inflation and deflation cycles. Moreover, cells may be of varying size. For example, cells in a device designed for a child may be smaller than cells in a device designed for an adult. However, the compression pump 105 may have a relatively fixed flow rate. As such, modulation may be used to ensure that cell inflation is performed at a proper rate.

In an alternate embodiment, a cell valve, such as 125a, may include a variable aperture, which may be used to restrict the rate at which the pressure increases in the corresponding cell. A flow sensor such as 150a may monitor the fluid flow rate into the cell. The data from the flow sensor may be provided to controller 145 so that the controller may be able to adjust the aperture in the cell valve. In another embodiment, a cell valve such as 125a may incorporate a one-way valve. For example, if valve 125a is opened to allow cell A to be filled by common manifold 140 or fill manifold 141, and then valve 125b is opened to allow cell B to be pressurized, a one-way valve incorporated in valve 125a will prevent transient depressurization of cell A when valve 125b is opened to initially evacuated cell B. In another alternate embodiment, a compression pump 105 that operates with a variable flow rate may be used. Additional methods of modulating pressure may also be performed and will be apparent to one of ordinary skill in the art based on this disclosure.

When the cell reaches an appropriate pressure, the controller 145 may close the cell valve 125a corresponding to the cell.

A protocol may also incorporate one or more cell exhaust phases. As a non-limiting example of such an exhaust phase, the following operating sequence may occur. One or more cell valves 125a-N may be opened along with the exhaust valve 130, thereby allowing the one or more cells to be in fluid communication with either the vacuum source 110 or the atmosphere 135. In an embodiment incorporating a common manifold 140, one or more of the cell valves 125a-N may open to the common manifold. In an embodiment having independent fill manifold 141 and exhaust manifolds 142, the one or more cell valves 125a-N may be configured to open the cells to communicate with the exhaust manifold 142 only. In an embodiment, a cell valve, such as 125a, connected to a cell affixed to a distal portion of the patient, may be opened or remain open to the exhaust manifold 142 or common manifold 140 for deflation while cell valves associated with more proximal cells are closed to that manifold. The cell (e.g. cell A) connected to the open cell valve (e.g. 125a) may deflate as a result of being connected to the vacuum source 110 or atmosphere 135. The cell pressure may be monitored by the controller 145 via transducer 115 for a common manifold configurations or transducer 115' for independent manifold configurations, a pressure sensor 155a associated specifically with that cell, or by both.

In an embodiment, the amount of pressure sensed by the transducer 115 or transducer 115' may differ from the cell pressure at a particular cell. For example, pressure losses may occur between the transducer 115 (or 115') and a cell. Accordingly, the controller 145 may access a lookup table to determine the threshold at which the pressure sensed by the transducer 115 (or 115') is appropriate to close the cell valve 125a-N corresponding to the cell.

In another embodiment of an exhaust phase, an opened cell valve, such as 125a, may be modulated to control the exhaust rate of the corresponding cell. The opened cell valve may be modulated based on time and/or pressure. For example, a cell valve that is being modulated on a time basis may be opened for a first period of time and closed for a second period of time as the cell is deflating. Alternately, a cell valve that is being modulated on a pressure basis may be opened while the cell pressure decreases and closed for a period of time during the exhaust cycle. The pressure decrease may be determined by measuring an initial cell pressure before opening the cell valve and the deflated cell pressure as the cell valve is open. When the difference between the initial cell pressure and the cell pressure is substantially equal to a specific value, the cell valve may be closed. The duty cycle at which the cell valve is modulated may be any value and may be specifically programmed by a user or clinician. The controller 145 may determine when to open and close the cell valve. For pressure-based modulation, any one or more of transducers 115, 115', or cell specific pressure sensors 155 may provide pressure data to the controller 145 to assist in determining when to open and/or close the cell valve during modulation.

Modulation may be performed to ensure that the cell pressure does not decrease too quickly, which could cause a reverse gradient. Moreover, cells may be of varying size. For example, cells in a device designed for a child may be smaller than cells in a device designed for an adult. However, the vacuum source 110 may have a relatively fixed flow rate, and venting to atmosphere 135 may occur due to unregulated, passive exhaust. As such, modulation may be used to ensure that cell deflation is performed at a proper rate.

In an alternate embodiment, a cell valve, such as 125a, may include a variable aperture, which may be used to restrict the rate at which the pressure decreases in the corresponding cell. A flow sensor such as 150a may monitor the fluid flow rate into the cell. The data from the flow sensor may be provided to controller 145 so that the controller may be able to adjust the aperture in the cell valve. In another embodiment, a cell valve such as 125a may incorporate a one-way valve. For example, if valve 125a is opened to allow cell A to be evacuated by exhaust manifold 142, and then valve 125b is opened to allow cell B to be evacuated, a one-way valve incorporated in valve 125a will prevent transient re-pressurization of cell A when valve 125b is opened to previously pressurized cell B. In another alternate embodiment, a vacuum source 110 that operates with a variable flow rate may be used. Additional methods of modulating pressure may also be performed and will be apparent to one of ordinary skill in the art based on this disclosure.

When the cell reaches an appropriate pressure, the controller 145 may close the cell valve 125a corresponding to the cell.

It may be appreciated that a therapeutic protocol may be composed of any variety of sequences of cell inflation and deflation steps. Cells may be inflated and deflated in a specific order, and multiple cells may be inflated or deflated either in synchrony or in a staggered fashion. The cells may be held at a particular inflation or deflation pressure for a specific amount of time. In addition, a specific protocol may be repeated with some lag time between repeats. Alternatively, a first protocol may be followed by a second and different protocol.

In one embodiment of a protocol, a plurality of cell valves 125a-N may be opened simultaneously to inflate the plurality of respective cells simultaneously. As the pressure in each cell surpasses a corresponding threshold, the controller 145 may close the cell valve 125a-N for the cell. The pressure thresholds for all the cells may be identical or they may differ. For example, the pressure threshold for a cell at a distal position on a patient may be higher than a cell more proximally located. As a result, a pressure gradient may be developed by the cells from a greater pressure at the distal point, to a lesser pressure at the proximal point. The cells may then be deflated simultaneously until they all reach an ambient pressure. Alternatively, only selected cells may be deflated.

In an another embodiment of a protocol, the cell valves 125a-N may not be opened simultaneously when the cells are deflated, but rather may be opened in a staggered fashion. In an embodiment based on the common manifold configuration, fill valve 120 may be closed, and exhaust valve 130 may be opened to either the vacuum source 110 or to atmosphere 135. A first cell valve, such as 125a, may be opened to release the pressure in the corresponding cell. After a short period of time elapses, such as about 1 second, a second cell valve, such as 125b, may be opened to release the pressure in the corresponding cell. The process may be repeated until each cell valve 125a-N has been opened.

In an embodiment of a protocol using modulation, a plurality of cell valves 125a-N may be modulated simultaneously. At any given time, one or more cell valves may be opened and/or closed according to a modulation schedule. For example, for a time-based modulation scheme having a 50% duty cycle, half of the cell valves 125a-N may be open and half of the cell valves may be closed at any time.

Figure 2:
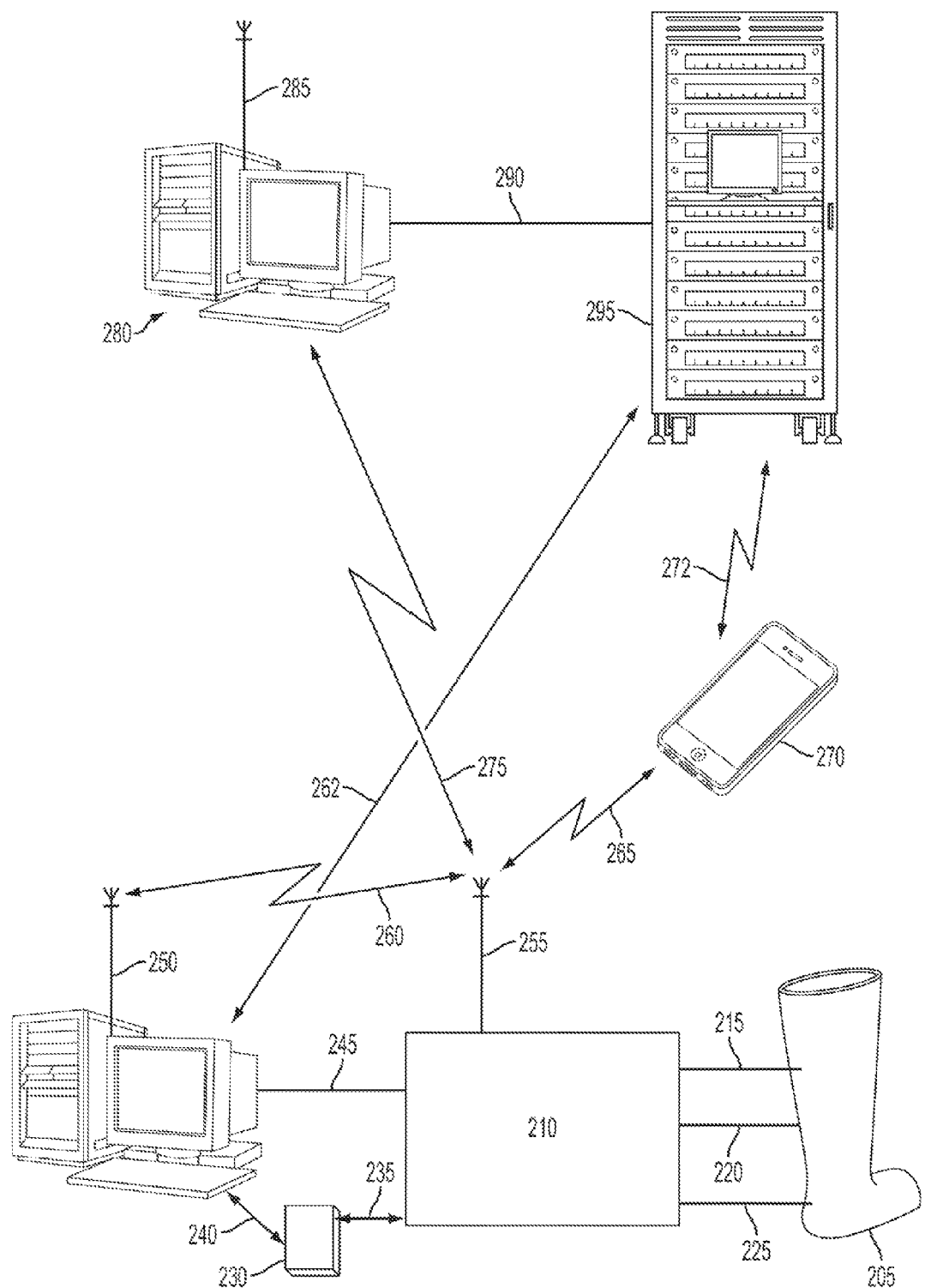
FIG. 2 depicts an illustrative compression therapy system and some data exchange paths between the therapy system and possible recipients of the related therapy data in accordance with an embodiment.

FIG. 2 depicts illustrative data communication exchanges between a compression system and a variety of electronic devices. The compression system may include a controller system 210 and at least one compression sleeve (such as a boot) 205. The compression sleeve 205 may be designed to deliver compression therapy to specific body parts. As some non-limiting examples, there may be a torso sleeve, an arm sleeve, a shoulder sleeve, a thigh sleeve, a calf sleeve, an ankle sleeve, a back sleeve, a chest sleeve, a buttocks sleeve, a genital sleeve, or a foot sleeve. The individual sleeves may be combined into a single unit such as a sleeve comprising a torso element, a shoulder element, and an arm element. Alternatively, a sleeve may include a combination of a thigh element, a calf element, an ankle element, and a foot element. In another embodiment, a patient may wear more than one sleeve to deliver compression therapy to non-contiguous body parts such as the chest and lower arm. Other combinations of sleeves or sleeve elements may also be anticipated. The controller system may include the pneumatic components as illustrated in FIGS. 1a, b. Thus, sleeve 205 may receive air pressure from manifold lines 215, or vacuum from an exhaust manifold 220. Sleeve 205 may also provide sensor data over a number of sensor lines such as 225. As non-limiting examples, the sensor data may include one or more of individual cell pressure, cell volumetric data based on cell surface deformation, cell volume, the temperature within the sleeve, or data related to a pulse sensed from a patient body part inserted into the sleeve. In one embodiment, it may be desirable for a patient to wear an undergarment beneath the compression sleeve, to reduce perspiration build-up in the sleeve and prevent patient skin chafing. The undergarment may include a tag such as a small magnet, a barcode tag, or a radiofrequency identifying tag. The sleeve may then include a sensor for the undergarment tag, such as an optical sensor, a magnetic sensor or a radiofrequency sensor. The sensor data may be incorporated into operational therapy data stored by one or more memory devices within the controller. The memory devices may include transitory (e.g. RAM) or non-transitory (e.g. ROM) memory devices. In some non-limiting examples, the operational therapy data may be stored in a removable SD card 230, a writable CDROM, a writable DVD, a USB flash drive memory device, a flash memory card, or a miniature tape drive, among others.

The operational therapy data may be transmitted to any one or more parties interested in the patient's compliance with a therapy protocol. Non-limiting examples of compliance data recipients may include any one or more of a manufacturer or supplier of the equipment, a medical practitioner such as a physician and/or therapist, a medical facility, a medical insurance provider, family members, a clinical therapy follow-up repository, and/or an accountable care organization.

In one embodiment, the raw operational therapy data may be supplied to the interested parties in order to determine patient compliance. In another embodiment, the operational therapy data may be compared to some known standard data, and the difference between the operational data and the standard data may be supplied as an indicator or metric of patient compliance. In yet another embodiment, a standardized report including summary data for a given therapeutic session may be supplied. Such a report may include one or more of a date and time of the beginning of a therapy session, a length of time of the therapy session, and a compliance metric demonstrating that the patient was actually using the compression therapy system during the session. The compliance metric may be calculated, at least in part, based on the standard data. In still another embodiment, the controller may provide a status code on an output device to the patient after the patient presses a push-button to indicate that a therapy session has been completed. The status code may incorporate date, time, and a compliance metric in a manner that the user may not be able to decode. The patient may then contact a recipient of the data either via e-mail, telephone, or by entering the status code into a recipient-controlled website, thereby providing the compliance metric or status value to the recipient.

In one embodiment, the standard data may be calculated as an average of data from a number of individual users of the compression therapy device using a common therapy protocol. In another embodiment, the standard data may be obtained from the patient/user of a therapy device under supervised therapy conditions.

The compliance data—as a stream of operational data, difference data, report, compliance metric, or status code—may be presented to a recipient across a number of communication channels. In one embodiment, the compliance data may be stored in an SD card 230 or other removable memory device such as a USB flash drive, while the card is associated with the controller 235. The data may then be uploaded 240 to a patient based computer 247 or other electronic device. The electronic device 247 may communicate the data via a wireless connection or a wired connection 262 to a server 295. In an alternative embodiment, the controller 210 may include a wireless communication interface 255. In one example, the wireless communication interface 255 may communicate over a wireless interface 250 to the patient's own electronic device 247. In this manner, the operational data may be transmitted from the controller to the patient computer 260. In yet another example, a wired interface between the controller and the user computer 247 may permit wire-based communication transfer 245. In still another embodiment, controller may have a personal network wireless interface 255 that may communicate 265 through a cell phone 270 to a data server 295. In still another embodiment, the controller wireless communication link 255 may transmit 275 data directly to a wireless interface 285 of a remote electronic device 280. The controller 210 may convey this information to the recipients after each therapy session, or only after sessions in which the patient compliance has been detected as being less than complete compliance. It may be appreciated that the communications methods disclosed above are merely examples, and may not be taken as limiting the communication of operational therapy data and/or a compliance metric between the controller 210 and a recipient of the data.

Figure 3:
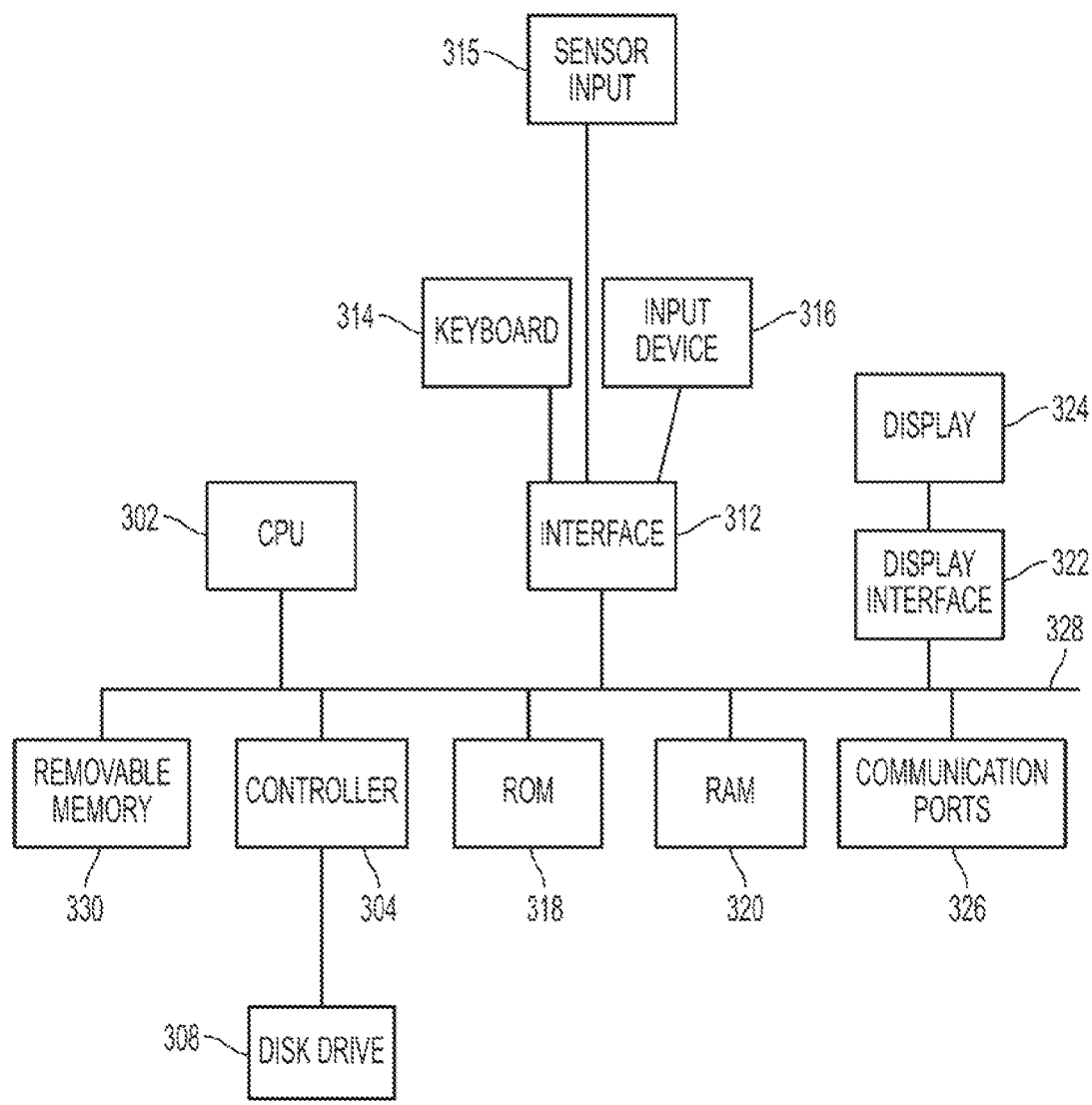
FIG. 3 is a block diagram illustrative of hardware that may be used to contain or implement program instructions in accordance with an embodiment.

FIG. 3 is a block diagram of an embodiment of hardware that may be used to contain or implement program instructions for controller 145. Some or all of the below-described hardware may be incorporated in the controller 145. Referring to FIG. 3, a bus 328 may serve as the main information highway interconnecting the other illustrated components of the hardware. CPU 302 is the central processing unit of the system, performing calculations and logic operations required to execute a program. Read only memory (ROM) 318 is one example of a static or non-transitory memory device, and random access memory (RAM) 320 is one example of a transitory or dynamic memory device.

A controller 304 may interface the system bus 328 with one or more optional disk drives 308. These disk drives may include, for example, external or internal DVD drives, CD ROM drives, or hard drives.

Program instructions may be stored in the ROM 318 and/or the RAM 320. Optionally, program instructions may be stored on a computer readable medium such as a compact disk or a digital disk or other recording medium, a communications signal or a carrier wave. Additionally, operational therapy data may be stored on a removable memory devices 330 that may include, as non-limiting examples, a removable disc, a removable card, a removable memory stick, a flash drive, a removable SIM chip, a writable CD ROM or DVD disk, and/or a miniature data tape. Such devices may be used to transfer data from the controller to another data receiving device such as a home computer.

An optional display interface 322 may permit information from the bus 328 to be displayed on the display 324 in audio, graphic or alphanumeric format. Additional output interface devices may include a printer, a barcode printer, an LCD panel device, a touch screen device, an audio device, an LED panel, an OLED panel device, one or more individual LEDs, either as separate displays or grouped together, and a haptic device. Communication with external devices may occur using various communication ports 326. For example, communication with the fill valve 120, exhaust valve 130, and/or the cell valves 125a-N may occur via one or more communication ports 326. Controller 145 may also provide command data over communication ports 326 to valves 120, 130, and 125a-N to direct their respective operations.

In addition to the components disclosed above, the hardware may also include an interface 312 which allows for receipt of data from input devices such as a keyboard 314 or other input device 316 such as a touch screen, a mouse, remote control, pointing device, pushbutton, haptic device, a voice recognition device, a proximity sensor, a motion detection sensor, a multi-axis accelerometer, a directional pad, and/or joystick. In addition, transducers 115 and 115', pressure sensors 155a-N, flow sensors 150a-N, as well as sensors communicating data related to the change in shape or volume of the cells, cell or sleeve temperatures, or sensors to detect the pulse associated with a body part inserted into a sleeve may communicate sensor input 315 through interface 312 to bus 328.

In an embodiment, the controller 145 may store and/or determine settings specific to each cell. For example, the controller 145 may determine one or more pressure thresholds for each cell. Moreover, the controller 145 may prevent the pneumatic compression device from being used improperly by enforcing requirements upon the system. For example, the controller 145 may be programmed so that distal cells in a therapeutic protocol are required to have higher pressure thresholds than proximal cells. The controller may override instructions received from a user via the user interface that does not conform to such pressure threshold requirements. In an embodiment, the pressure thresholds of one or more cells may be adjusted to meet the pressure threshold constraints.

In a further embodiment, controller 145 may provide a compression device user with an interface to permit the user to program the control to provide a variety of therapeutic protocols for patients. The interface may be displayed on the control display, such as a flat panel display. Input devices such as a mouse, keypad, or stylus may be used by the user to provide data to define a particular therapeutic protocol. In addition, a push-button device be activated by a user to indicate that data from the controller may be transmitted to a receiving unit such as a computer, cell phone, or wireless hot-spot. The controller may record the protocols on a memory or disk device for future use. In one embodiment of the controller, a user may be presented with a list of previously stored therapeutic protocols from which to choose for a particular patient. In another embodiment, a user may define a therapeutic protocol for a patient on an as-needed basis. In another embodiment, a user may choose a stored protocol and modify it.

In addition to storing protocols, the controller 145 may also record sensor readings obtained during a particular therapy session. Such sensors may include pressure sensors, timing sensors, fluid flow sensors, temperature sensors, inflatable cell material deformation sensors, and other. Sensor readings may include, without limitation, the time a sensor reading is made, cell pressures, cell volumes, cell inflation data, air or vacuum air flow values, and/or temperatures taken from an interior of the sleeve or compression device. The controller may also record patient related data such as blood pressure, EKG, or blood oxygen saturation levels measured during a therapeutic session, as well as a date and time for the session. The controller may also record therapy notes entered by the user.

Although not illustrated in FIG. 3, controller 145 may also include a number of communications interfaces to a wireless local area network, a localized personal area network (such as a Bluetooth connection or ZigBee connection), or a telephony device. Such communication devices may include, without limitation, an Ethernet connection device connected to a computing device, an infrared connecting device connected to a computing device, and a serial connection device connected to a computing device. Telephony devices may include, without limitations, cell phones, landline phones, voice modems, TRx devices, fax machines, and other communications devices based on telephone technology. Such communication interfaces may permit the controller to be monitored remotely by a clinician to obtain performance data or patient compliance data. Such communication interfaces may also permit a remote clinician to program the controller. In one embodiment, a cell phone may have an application that may bring up a user-friendly programming interface to permit ease of reprogramming. Alternatively, a remote computer may display a web-enabled display for programming, data assessment, and/or analysis.

Figure 4:
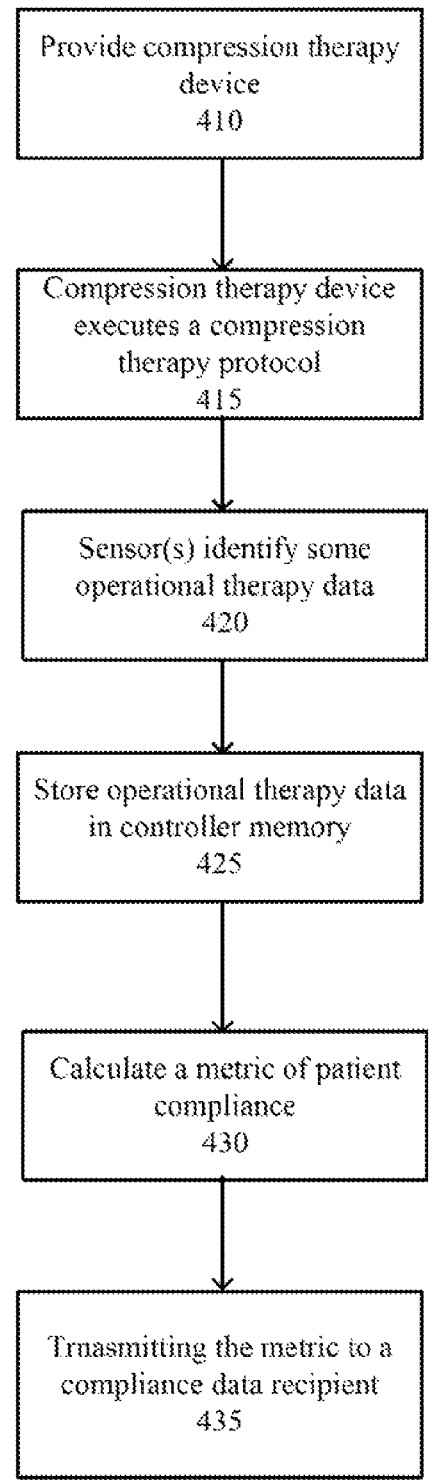
FIG. 4 is a flow chart illustrative of a method of determining patient use compliance of a therapy system in accordance with an embodiment.

FIG. 4 discloses a flow chart of one embodiment of a method of determining use compliance of a compression therapy device by a patient. A compression therapy device, as substantially disclosed above, may be provided to a patient 410. The compression therapy device may include an inflatable compression sleeve, a source of fluid—such as a gas—for inflating the sleeve, and a controller unit to control the inflation and deflation of the sleeve and/or the individual cells comprising the sleeve. The controller may include one or more sensors associated with the sleeve, sensors associated with the inflation and deflation devices for the sleeve, at least one non-transitory memory device, and at least one communication device. The controller may also include user input devices. The patient may then cause the compression therapy device to initiate a therapy protocol 415.

During the therapy protocol, sensors associated with the compression device may acquire and identify relevant operational therapy data from the compression device sensors 420. The operational therapy data may include, without limitation, pressures associated with the cells in the compression sleeve, air flow into and out from the cells, data associated with the volume attained by the cells during inflation and deflation during a therapy session, the temperature in the interior of the compression sleeve, and data associated with the pulse of the patient's body part inserted into the sleeve. The operational therapy data may also include a start time for a therapy protocol, a stop time for the therapy protocol, a rate of inflating at least one inflatable cell in the compression sleeve, a rate of deflating at least one inflatable cell in the compression sleeve, a time course of inflating at least one inflatable cell in the compression sleeve, a time course of deflating at least one inflatable cell in the compression sleeve, a time course of a pressure within at least one inflatable cell in the compression sleeve, a rate of pressurizing at least one inflatable cell in the compression sleeve, a start time of a compression therapy session, and a stop time of a compression therapy session. The operational therapy data may then be stored in the controller memory, such as a non-transitory memory including either a non-removable memory or a removable memory 425.

In one embodiment, the controller may then calculate a metric of patient compliance based, at least in part, on the operational therapy data 430. The calculation may include calculating a difference between the operational therapy data and a standard therapy data set. In one embodiment, the standard therapy data set may be derived from an average of operational therapy data obtained from a number of patients undergoing the same therapy protocol. In another embodiment, the standard therapy data set may be derived from data taken of the patient during a supervised therapy session while undergoing the same therapy protocol. The supervised data set may be taken while a physician or therapist assures that the patient is using the compression therapy device correctly, and uses it for a complete therapy session. An average of several sessions may be calculated to insure statistical accuracy and account for normal variation in therapy device use. The standard therapy data may also depend, at least in part, on the type of the compression sleeve used by the patient, either size, construction, or part of the body for which it may be designed. The standard therapy data set may be stored in a memory storage device of the controller. The metric may include one or more of a numerical value, a text string, or a graphical representation, either separately or in combination.

The compliance metric may represent, as examples, a binary report on compliance for a particular therapy session (patient complied/did not comply), or a probability value that a patient was compliant during a therapy session. The metric may be calculated based on the actual sensor data taken during a therapy session compared to expected sensor data for a compliant patient during a session. Data related to expected sensor results may include the rates of cell filling, time for cell or sleeve inflation, final cell pressures, or final cell volumes during a particular protocol. If a patient body part (such as a leg) is not in the sleeve during a protocol, or the patient is not properly affixing the sleeve about the body part, it may be expected that the inflatable cells will not meet the resistance of the body part during inflation. Consequently, the fluid flow rate into the cells may be greater at the end of an inflation cycle if there is no body part to resist the increased fluid flow. Related measurements may include the final cell pressure (less than expected if the body part was within the sleeve), and final cell volume (greater than expected).

In addition to sensors and data related to the inflation and deflation of the cells in the compression device, other sensors may be provided to obtain data related to patient compliance. For example, a temperature sensor may be associated with the sleeve. Thus, a session with a non-compliant patient may result in the temperature sensor recording ambient air temperature as opposed to the temperature of the patient's body part within the sleeve. In another embodiment, the patient may receive an undergarment to be worn under the compression sleeve. The undergarment may include one or more indicator devices such as a readable (barcode) tag, a radiofrequency identification device (RFID), or one or more small magnets. Appropriate optical, radiofrequency, and/or magnetic sensing devices may be included with the compression sleeve to check if the undergarment was being worn during a therapeutic session. An additional embodiment may include a strain gauge associated with one or more inflatable cells. A strain gauge may measure the deformation of the cell surface and may indicate the presence or absence of a body part which could deform the surface of the cell upon inflation. Similarly, a sensor capable of recording a patient's pulse may not record a pulse if the body part is not within the sleeve. It may be appreciated that other measurements from sensors associated with the inflatable sleeve may be able to distinguish a compliant patient from a non-compliant patient.

After the metric of patient compliance has been calculated, the metric may be transmitted to at least one compliance data recipient 435. The manner in which the compliance metric is transmitted can be based on a number of different transmission routes as disclosed above. In one embodiment, the communication device of the controller may transmit the metric directly via a local or wide area wireless network to a computing device such as a server controlled at least in part by a compliance data recipient. In another embodiment, the metric may be transmitted via a localized personal area network to a cell phone that can communicate with a recipient. In another embodiment, the controller communication interface may include a serial link to a telephone device for similar communication to the recipient. The controller may be used to transmit the metric over either an ethernet connection, wireless RF connection, or IR connection to a patient's personal computing device. The personal computing device may store the metric data until the user transmits it to the recipient by uploading a file to a server, e-mailing the data to an e-mail address, or entering the data into a website, any one or more of which may be controlled at least in part by the recipient. In yet another embodiment, the data may be stored by the controller on a removable memory or data storage device (such as a SIM chip). The removable memory device may then be put into data communication with the patient's personal computing device, and the data within the removable memory storage device may be provided to the recipient by e-mail, file transfer, or website entry. In still another embodiment, the controller may retain the one or more compliance metrics after a therapy session until the patient activates a pushbutton or other input device. Upon receipt of the patient input, the controller may provide the patient with the compliance metric, for example by an output display, that the patient may relay to the compliance data recipient either by e-mail, by entry into a website, or by phone. In another embodiment, the patient may request the controller to print a copy of a compliance metric or other report regarding the therapy session, and the patient may transmit the printed copy by mail to at least one compliance data recipients Although it has been disclosed above that the compliance data may be received by one or more compliance data recipients, it may be understood that the data may also be shared among several such recipients. For example, a provider of the compression therapy system may receive the compliance data or metric and then relay that information to a provider of health care insurance or to a therapist monitoring the patient's progress. The initial recipient of the compliance data may forward the data intact or reduced to a summary report to the secondary recipients. The report may include one or more of text, numerical data, charts, and/or graphs. The report to the secondary recipients may include compliance data for a single patient during a single therapy session, a single patient including compliance data from multiple therapy sessions, or multiple patients including compliance data from one or more therapy sessions.

It is understood that the calculation of the compliance metric is not necessarily restricted to the therapy system controller, and that standard therapy data need not be located only in the memory of the controller. Alternative embodiments anticipate that the raw operational therapy data may be transmitted to a computing device (such as a server) controlled at least in part by one or more of the compliance data recipients. The recipient controlled device may then calculate the compliance metric based at least in part on the received raw operational data and a standard therapeutic data set located in memory associated with the recipient controlled computing devices.

In one non-limiting embodiment, the pneumatic compression device may be portable. In an embodiment, the pneumatic compression device may include a user interface that enables the user to interact with the controller 145. For example, the user interface may include a display and one or more input devices, such as a keypad, a keyboard, a mouse, a trackball, a light source and light sensor, a touch screen interface and/or the like. The one or more input devices may be used to provide information to the controller 145, which may use the information to determine how to control the fill valve 120, exhaust valve 130, and/or the cell valves 125*a*-N.

It will be appreciated that the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A method of monitoring a therapy compliance by at least one patient, the method comprising:
   providing a compression therapy device comprising
      an inflatable compression sleeve comprising a plurality of cells in fluid communication with an exhaust valve that is operably connected to a compressor configured for selectively inflating the plurality of cells in the inflatable compression sleeve and to a vacuum source configured for selectively deflating the plurality of cells, and
      a controller for controlling the inflation of the compression sleeve, the controller comprising at least one sensor associated with the compression sleeve, at least one non-transitory memory storage device, and at least one communication device;
   initializing the compression therapy device, wherein initializing comprises opening the exhaust valve and depressurizing the plurality of cells by the vacuum source to reach an initial minimum pressure threshold;
   closing, by the controller, the exhaust valve upon reaching the initial minimum pressure threshold;
   next, executing at least one compression therapy protocol with the compression therapy device;
   identifying, by the at least one sensor, operational therapy data during the at least one compression therapy protocol, wherein identifying the operational therapy data comprises:
      measuring, by the at least one sensor, sensor data comprising information related to performance variables related to operation of the plurality of cells from the initial minimum pressure threshold for each of the plurality of cells to completion of the at least one compression therapy protocol;
   storing, by the at least one memory storage device, the operational therapy data at the memory storage device, wherein the operational therapy data comprises at least the sensor data;
   calculating, by the controller, a metric of patient compliance based at least in part on the operational therapy data, wherein calculating the metric of patient compliance comprises:
      identifying an existing therapy data set,
      calculating a difference between the operational therapy data and the existing data set, and
      determining the metric of patient compliance based upon the calculated difference; and
   transmitting, by the controller, the metric of patient compliance to at least one compliance data recipient.

2. The method of claim 1, wherein the inflatable compression sleeve comprises one or more of the following: a chest sleeve, a foot sleeve, an ankle sleeve, a calf sleeve, a lower leg sleeve, a thigh sleeve, an upper leg sleeve, a lower arm sleeve, an upper arm sleeve, a wrist sleeve, a hand sleeve, a chest sleeve, a single shoulder sleeve, a back sleeve, an abdomen sleeve, a buttocks sleeve, a genital sleeve, and combinations thereof.

3. The method of claim 1, wherein the at least one sensor comprises one or more of the following: a pressure sensor, a timing sensor, a flow sensor, a temperature sensor, a material deformation sensor, an optical sensor, a magnetic sensor, a radiofrequency sensor, and a strain gauge.

4. The method of claim 1, wherein the at least one memory storage device is removable.

5. The method of claim 4, wherein the at least one memory storage device is one or more of the following: a removable disc, a removable card, and a removable memory chip.

6. The method of claim 1, wherein the operational therapy data comprises a temperature of an interior of the compression sleeve and one or more of the following: a start time for the therapy protocol, a stop time for the therapy protocol, a rate of inflating at least one inflatable cell in the compression sleeve, a rate of deflating at least one inflatable cell in the compression sleeve, a time course of inflating at least one inflatable cell in the compression sleeve, a time of inflating the compression sleeve, a time course of deflating at least one inflatable cell in the compression sleeve, a time course of a pressure within at least one inflatable cell in the compression sleeve, and a rate of pressurizing at least one inflatable cell in the compression sleeve.

7. The method of claim 1, wherein the at least one communication device is one or more of the following: an ethernet connection device to connect to a computing device, an infrared connection device to connect to a computing device, a serial connection device, a wireless local area network device, a localized personal area network device, and a telephony device.

8. The method of claim 1, wherein the controller further comprises at least one user input interface device comprising one or more of the following: a touch screen device, a mouse, a push button, a voice recognition device, a joystick, a directional pad, a proximity sensor, a motion detection sensor, a multi-axis accelerometer, and a keyboard.

9. The method of claim 1, wherein the controller further comprises at least one user output interface device comprising one or more of the following: an LCD panel device, a touch screen device, an audio device, an LED panel device, one or more LEDs, a haptic device, and an OLED panel device.

10. The method of claim 1, wherein the compression therapy protocol is executed while the at least one patient is wearing the compression sleeve.

11. The method of claim 1, wherein the metric of patient compliance comprises one or more of the following: at least one numerical value, at least one text string, at least one graphical representation, and combinations thereof.

12. The method of claim 1, wherein calculating a metric of patient compliance further comprises:
   providing a standard therapy data; and comparing the operational therapy data with the standard therapy data.

13. The method of claim 12, wherein the standard therapy data are stored in the at least one memory storage device of the controller.

14. The method of claim 12, wherein the standard therapy data are stored in a memory storage device associated with a computing device controlled at least in part by the at least one compliance data recipient.

15. The method of claim 12, wherein calculating a metric of patient compliance comprises calculating a difference between at least a portion of operational therapy data and at least a portion of standard therapy data.

16. The method of claim 12, wherein providing a standard therapy data comprises obtaining one or more of the following:
   an average of a plurality of operational therapy data generated by one or more compression therapy devices used by a plurality of patients undergoing the at least one compression therapy protocol; and at least one operational therapy data generated by the compression therapy device used by the patient undergoing the at least one compression therapy protocol under supervision by a therapy supervisor.

17. The method of claim 12, wherein the standard therapy data are based at least in part on a type of inflatable compression sleeve.

18. The method of claim 1, wherein calculating the metric of patient compliance further comprises calculating the metric of patient compliance by the controller.

19. The method of claim 1, wherein calculating the metric of patient compliance further comprises calculating the metric of patient compliance by a computing device controlled at least in part by the at least one compliance data recipient.

20. The method of claim 1, wherein transmitting the metric of patient compliance comprises:
   activating, by the at least one patient, a user input interface device associated with the controller;
   receiving, by the at least one patient, the metric of patient compliance from a user output interface device associated with the controller; and
   communicating, by the at least one patient, the metric of patient compliance to the at least one compliance data recipient.

21. The method of claim 1, wherein transmitting the metric of patient compliance comprises one or more of the following:
   removing a removable data storage device from the controller and placing the removable data storage device in data communication with a computing device that is further in data communication with an electronic device controlled at least in part by the at least one compliance data recipient;
   transmitting the metric over an Ethernet connection to a computing device in data communication with a website controlled at least in part by the at least one compliance data recipient;
   transmitting the metric via an infrared connection device to a computing device in data communication with a website controlled at least in part by the at least one compliance data recipient;
   transmitting the metric via a serial connection to a computing device in data communication with a website controlled at least in part by the at least one compliance data recipient;
   transmitting the metric via a serial connection to a telephony device in data communication with the at least one compliance data recipient;
   transmitting the metric via a localized personal area network to a telephony device in data communication with the at least one compliance data recipient;
   transmitting the metric via a wireless local area network to an electronic device controlled at least in part by the at least one compliance data recipient; and
   mailing a printed copy of the metric to the at least one compliance data recipient.

22. The method of claim 1, wherein the compliance data recipient is one or more of the following: a supplier of the compression therapy device, a manufacturer of the compression therapy device, a medical facility, a medical practitioner, a therapist, a provider of medical insurance, and a patient family member.

23. The method of claim 1, further comprising transmitting the operational therapy data to the at least one compliance data recipient.

24. The method of claim 1, further comprising:
   receiving, by a first compliance data recipient, a plurality of metrics of patient compliance, wherein each metric is received from one of a plurality of patients;
   compiling a report, by the first compliance data recipient, based at least in part on the plurality of metrics; and
   transmitting, by the first compliance data recipient to a second compliance data recipient, the report.

25. The method of claim 1, further comprising:
   receiving, by a first compliance data recipient, a plurality of metrics of patient compliance, from the patient;
   compiling a report, by the first compliance data recipient, based at least in part on the plurality of metrics; and
   transmitting, by the first compliance data recipient to a second compliance data recipient, the report.

* * * * *